United States Patent
Hill

(10) Patent No.: US 7,919,059 B2
(45) Date of Patent: *Apr. 5, 2011

(54) VAPORIZED HYDROGEN PEROXIDE DECONTAMINATION SYSTEM WITH CONCENTRATION ADJUSTMENT MODE

(75) Inventor: Aaron L. Hill, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 237 days.

This patent is subject to a terminal disclaimer.

(21) Appl. No.: 11/741,069

(22) Filed: Apr. 27, 2007

(65) Prior Publication Data

US 2008/0267818 A1 Oct. 30, 2008

(51) Int. Cl.
*A61L 2/00* (2006.01)
*A61L 9/00* (2006.01)
*A61L 2/18* (2006.01)
*A61L 2/20* (2006.01)

(52) U.S. Cl. .......... 422/298; 422/292; 422/295; 422/28; 422/33

(58) Field of Classification Search .................. 422/298, 422/292
See application file for complete search history.

(56) References Cited

U.S. PATENT DOCUMENTS

| | | | |
|---|---|---|---|
| 4,204,037 A | 5/1980 | Frosch et al. | 435/3 |
| 4,241,010 A * | 12/1980 | Baran | 422/2 |
| 4,591,485 A | 5/1986 | Olsen et al. | 422/20 |
| 4,843,867 A | 7/1989 | Cummings | 73/23 |
| 4,863,688 A | 9/1989 | Schmidt et al. | 422/28 |
| 4,908,188 A | 3/1990 | Jefferis et al. | 422/111 |
| 4,952,370 A | 8/1990 | Cummings et al. | 422/28 |
| 4,956,145 A | 9/1990 | Cummings et al. | 422/28 |
| 5,020,481 A | 6/1991 | Nelson | 122/494 |
| 5,114,670 A | 5/1992 | Duffey | 422/24 |
| 5,122,344 A | 6/1992 | Schmoegner | 422/111 |
| 5,173,258 A | 12/1992 | Childers | 422/27 |
| 5,418,167 A | 5/1995 | Matner et al. | 435/288 |
| 5,492,672 A | 2/1996 | Childers et al. | 422/28 |
| 5,650,693 A | 7/1997 | Campbell et al. | 315/111.21 |
| 5,770,393 A | 6/1998 | Dalmasso et al. | 435/31 |
| 5,788,925 A | 8/1998 | Pai et al. | 422/3 |
| 5,866,356 A | 2/1999 | Albert et al. | 435/31 |

(Continued)

FOREIGN PATENT DOCUMENTS

WO WO 97/47331 12/1997

(Continued)

OTHER PUBLICATIONS

U.S. Appl. No. 11/421,265, filed May 31, 2006, Buczynski, entitled: Decontamination System With Air Bypass.

(Continued)

*Primary Examiner* — Sean E Conley
*Assistant Examiner* — Regina Yoo
(74) *Attorney, Agent, or Firm* — Kusner & Jaffe; Michael A. Centanni

(57) ABSTRACT

A decontamination system for decontaminating a region with a vaporized decontaminant, such as vaporized hydrogen peroxide. The concentration of the vaporized decontaminant within the region is modified in response to operating conditions. The decontamination system adjusts the concentration of the vaporized decontaminant in response to the monitored saturation concentration of the decontaminant, thereby preventing condensation of the vaporized decontaminant during a decontamination cycle. The decontamination system also adjusts the concentration of the vaporized decontaminant in order to minimize the time required to complete a successful decontamination operation.

10 Claims, 2 Drawing Sheets

U.S. PATENT DOCUMENTS

| | | | | |
|---|---|---|---|---|
| 5,872,359 | A | 2/1999 | Stewart et al. | 250/339.12 |
| 5,876,664 | A | 3/1999 | Childers et al. | 422/28 |
| 5,882,590 | A | 3/1999 | Stewart et al. | 422/28 |
| 5,906,794 | A | 5/1999 | Childers | 422/28 |
| 6,156,267 | A | 12/2000 | Pai et al. | 422/3 |
| 6,369,112 | B1 | 4/2002 | Xia | 514/635 |
| 6,379,615 | B1 | 4/2002 | Ogle | 422/28 |
| 6,387,648 | B1 | 5/2002 | Levi et al. | 435/26 |
| 6,428,746 | B1 | 8/2002 | Muscarella et al. | 422/3 |
| 6,455,272 | B1 | 9/2002 | Gillis | 435/31 |
| 6,513,378 | B1 | 2/2003 | Love, Jr. | 73/313 |
| 6,528,016 | B1 | 3/2003 | Kohler et al. | 422/28 |
| 6,718,077 | B1 | 4/2004 | Ferreira et al. | 385/12 |
| 6,787,105 | B2 | 9/2004 | Robbins | 422/22 |
| 6,803,728 | B2 | 10/2004 | Balasubramaniam et al. | 315/149 |
| 6,953,549 | B2 | 10/2005 | Hill et al. | 422/30 |
| 7,157,046 | B2 | 1/2007 | McVey et al. | 422/28 |
| 7,186,374 | B2 | 3/2007 | Zelina et al. | 422/28 |
| 7,238,330 | B2 | 7/2007 | Hill et al. | 422/292 |
| 7,252,800 | B2 | 8/2007 | Jacobs et al. | 422/33 |
| 2002/0114727 | A1 | 8/2002 | McVey et al. | 422/4 |
| 2002/0159915 | A1 | 10/2002 | Zelina et al. | 422/3 |
| 2003/0031589 | A1* | 2/2003 | Martin et al. | 422/28 |
| 2003/0063997 | A1 | 4/2003 | Fryer et al. | 422/3 |
| 2003/0138344 | A1* | 7/2003 | Mielnik et al. | 422/2 |
| 2003/0164091 | A1 | 9/2003 | Hill et al. | 95/90 |
| 2004/0076358 | A1 | 4/2004 | Ferreira et al. | 385/12 |
| 2004/0105758 | A1 | 6/2004 | Ross | 417/44.1 |
| 2004/0154965 | A1 | 8/2004 | Baum et al. | 210/85 |
| 2005/0079096 | A1 | 4/2005 | Brown-Skrobot et al. | 422/24 |
| 2005/0252274 | A1 | 11/2005 | Centanni | 73/23.2 |
| 2005/0274656 | A1 | 12/2005 | McKinney | 210/86 |
| 2005/0276723 | A1 | 12/2005 | Sundaram et al. | 422/28 |
| 2006/0008379 | A1 | 1/2006 | Mielnik et al. | 422/32 |
| 2006/0061953 | A1 | 3/2006 | Le | 361/684 |
| 2006/0088441 | A1 | 4/2006 | Hill | 422/30 |
| 2006/0099106 | A1 | 5/2006 | Watling et al. | 422/3 |
| 2006/0257877 | A1 | 11/2006 | Anderle et al. | 435/6 |
| 2007/0014691 | A1 | 1/2007 | Lin et al. | 422/62 |
| 2007/0098592 | A1 | 5/2007 | Buczynski et al. | 422/3 |
| 2008/0038166 | A1* | 2/2008 | Hill et al. | 422/292 |
| 2008/0267818 | A1 | 10/2008 | Hill | 422/28 |

FOREIGN PATENT DOCUMENTS

WO    WO 03/082355    10/2003

OTHER PUBLICATIONS

U.S. Appl. No. 11/463,608, filed Aug. 10, 2006, Hill, entitled: Modular Decontamination System.

U.S. Appl. No. 11/740,973, filed Apr. 27, 2007, Hill, entitled: Vaporized Hydrogen Peroxide Probe Calibration Rig.

U.S. Appl. No. 11/741,299, filed Apr. 27, 2007, Hill, entitled: Hydrogen Peroxide Vaporizer.

U.S. Appl. No. 11/838,327, filed Aug. 14, 2007, Hill, entitled: Method and Apparatus for Decontaminating a Region Without Dehumidification.

* cited by examiner

VAPORIZED HYDROGEN PEROXIDE DECONTAMINATION SYSTEM WITH CONCENTRATION ADJUSTMENT MODE

FIELD OF THE INVENTION

The present invention relates generally to the art of decontamination, and more particularly to a decontamination system that adjusts the concentration of a gaseous or vapor phase decontaminant in response to operating conditions.

BACKGROUND OF THE INVENTION

Decontamination methods are used in a broad range of applications, and have used an equally broad range of decontaminating agents. As used herein the term "decontamination" refers to the inactivation of bio-contamination, and includes, but is not limited to, sterilization and disinfection.

During a decontamination cycle of a typical hydrogen peroxide vapor decontamination system, an aqueous solution of hydrogen peroxide (e.g., about 30% to 59% hydrogen peroxide by weight) is injected into a vaporizer. The vaporizer vaporizes the aqueous solution of hydrogen peroxide, thereby generating a hydrogen peroxide vapor that is carried into a decontamination chamber by a carrier gas (e.g., air).

Gaseous and vaporous decontamination systems rely on maintaining certain process parameters in order to achieve a target decontamination assurance level. For hydrogen peroxide vapor decontamination systems, those parameters include, but are not limited to, the concentration of the hydrogen peroxide vapor, the degree of saturation, the temperature and pressure, and the exposure time. By controlling these parameters, the desired decontamination assurance levels can be successfully obtained while avoiding condensation of the hydrogen peroxide due to vapor saturation. In this regard, condensation of hydrogen peroxide is ordinarily not desired, since it can increase aeration time, cause corrosion, and lead to hazardous conditions. Some studies have also shown that condensation of the hydrogen peroxide may also inhibit the effectiveness of the hydrogen peroxide vapor.

Considering only temperature, condensation of hydrogen peroxide vapor occurs when an actual concentration of hydrogen peroxide vapor exceeds a saturation concentration of hydrogen peroxide vapor (also referred to herein as a "dew point" concentration) for a given temperature. In order to avoid condensation of the hydrogen peroxide vapor during a decontamination cycle, care must be taken to insure that the actual concentration of the hydrogen peroxide vapor in the decontamination chamber does not exceed the saturation concentration for the temperature in the decontamination chamber.

As previously indicated, atmospheres of hydrogen peroxide vapor typically include water vapor. The concentration of water vapor found in a vaporized hydrogen peroxide atmosphere depends on the initial concentration of water in the aqueous hydrogen peroxide-water mix and the degradation of vaporized hydrogen peroxide into water vapor during a decontamination cycle. In addition to showing a temperature dependency, the saturation concentration of hydrogen peroxide vapor is also a function of water vapor concentration. For example, it is observed in a vaporized hydrogen peroxide/water vapor atmosphere that the higher the actual concentration of water vapor, the lower the saturation concentration of hydrogen peroxide vapor.

The amount of vaporized hydrogen peroxide that can be produced per unit time (i.e., the injection rate) is limited by the capacity of the vaporizer. Therefore, in smaller enclosed areas, higher concentrations of hydrogen peroxide may be easily attained using the maximum injection rate. In larger enclosed areas (e.g., rooms), it may only be possible to obtain lower concentrations of hydrogen peroxide. As the concentration of hydrogen peroxide decreases, the time required to inactivate biocontamination increases exponentially.

Typically, a D-value is used to express the time (i.e., "decimal reduction time") required for a one log reduction of bioburden (i.e., a reduction in the viable microbial population by 90%). Accordingly, xD expresses the time required for x log reduction of bioburden. For example, to obtain a "kill" of 6 log reduction of Bacillus (Geobacillus) stearothermophilus using STERIS® VAPROX® Hydrogen Peroxide Sterilant, the object being decontaminated must be exposed to the STERIS® VAPROX® Hydrogen Peroxide Sterilant at a concentration of 250 ppm for an exposure time of 1.5 hours, or at a concentration of 400 ppm for an exposure time of 0.5 hours. However, once a decontamination cycle has commenced, two possible conditions may exist that prevent the use of the higher concentration (e.g., 400 ppm in the case of STERIS® VAPROX® Hydrogen Peroxide Sterilant) for the shorter exposure time. These two conditions are: (1) a hydrogen peroxide concentration that exceeds the dew point concentration, or (2) an inability to obtain the higher concentration level (e.g., 400 ppm) within the enclosure (e.g., room) due to vaporizer capacity limits (i.e., an insufficient maximum injection rate).

Existing decontamination systems lack control means for determining whether a condensation condition exists, and for determining an optimal concentration level from among of a plurality of possible concentration levels.

The present invention addresses these and other problems, and provides a decontamination system that includes feedback control to monitor condensation conditions and to determine an optimal concentration level.

SUMMARY OF THE INVENTION

In accordance with an embodiment of the present invention, there is provided a method for decontaminating a region with a vaporized decontaminant, the method comprising the steps of: establishing a first concentration level of the vaporized decontaminant and a first exposure time associate with the first concentration level; injecting the vaporized decontaminant into the region at an injection rate for obtaining the first concentration level of the vaporized decontaminant in the region; monitoring the actual concentration of the vaporized decontaminant in the region; determining the dew point concentration of the vaporized decontaminant in the region; determining a dew point margin indicative of whether the actual concentration of the vaporized decontaminant in the region is at least a predetermined amount below the dew point concentration of the vaporized decontaminant in the region; and modifying the injection rate if the actual concentration of the vaporized decontaminant in the region is not at least the predetermined amount below the dew point concentration of the vaporized decontaminant in the region.

In accordance with another aspect of the present invention, there is provided A method for decontaminating a region with a vaporized decontaminant, the method comprising the steps of: establishing a first concentration level of the vaporized decontaminant and a first exposure time associate with the first concentration level; establishing a second concentration level of the vaporized decontaminant and a second exposure time associated with the second concentration level, wherein the second concentration level is greater than the first concentration level; initiating a first timer when the actual concentration of the vaporized decontaminant in the region reaches the first concentration level, wherein the first timer indicates the total elapsed time that the actual concentration of the vaporized decontaminant in the region is at or above the first concentration level; and initiating a second timer when the actual concentration of the vaporized decontaminant in the region reaches the second concentration level, wherein the second timer indicates the total elapsed time that the actual concentration of the vaporized decontaminant in the region is at or above the second concentration level; determining a first time value indicative of the amount of time remaining until the first timer reaches the first exposure time; determining a second time value indicative of the amount of time remaining until the second timer reaches the second exposure time; and injecting vaporized decontaminant into the region at an injection rate for obtaining one of said first and second concentration levels based upon the difference between the first and second time values.

In accordance with still another aspect of the present invention, there is provided a vapor decontamination system for decontaminating a region, said system comprising: a generator for generating a vaporized decontaminant; a circulating system for supplying said vaporized decontaminant to said region; at least one humidity sensor providing a first signal indicative of moisture in the region; a temperature sensor providing a second signal indicative of the temperature in the region; at least one concentration sensor providing a third signal indicative of the concentration of the decontaminant in the region; input means for inputting into a controller one of: (a) a first concentration level and a first exposure time associated therewith, or (b) a first concentration level and a D-value indicative of a desired reduction of bioburden, wherein a first exposure time associated with the first concentration level is determined according to the D-value, a controller communicating with said generator to control the rate at which vaporized decontaminant is injected into the region, and receiving the first, second, and third signal, said controller operable to: (1) inject the vaporized decontaminant into the region at an injection rate for obtaining the first concentration level of vaporized decontaminant in the region; (2) monitor the actual concentration of the vaporized decontaminant in the region; (3) determine the dew point concentration of the vaporized decontaminant in the region; and (4) determine a dew point margin indicative of whether the actual concentration of the vaporized decontaminant in the region is at least a predetermined amount below the dew point concentration of the vaporized decontaminant in the region.

An advantage of the present invention is the provision of a decontamination system that monitors the saturation concentration of the hydrogen peroxide vapor in order to prevent condensation thereof.

Another advantage of the present invention is the provision of a decontamination system that allows a dew point margin to be established to prevent operating conditions that could result in condensation of hydrogen peroxide vapor.

Still another advantage of the present invention is the provision of a decontamination system that can operate at an optimal concentration level based upon operating conditions.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
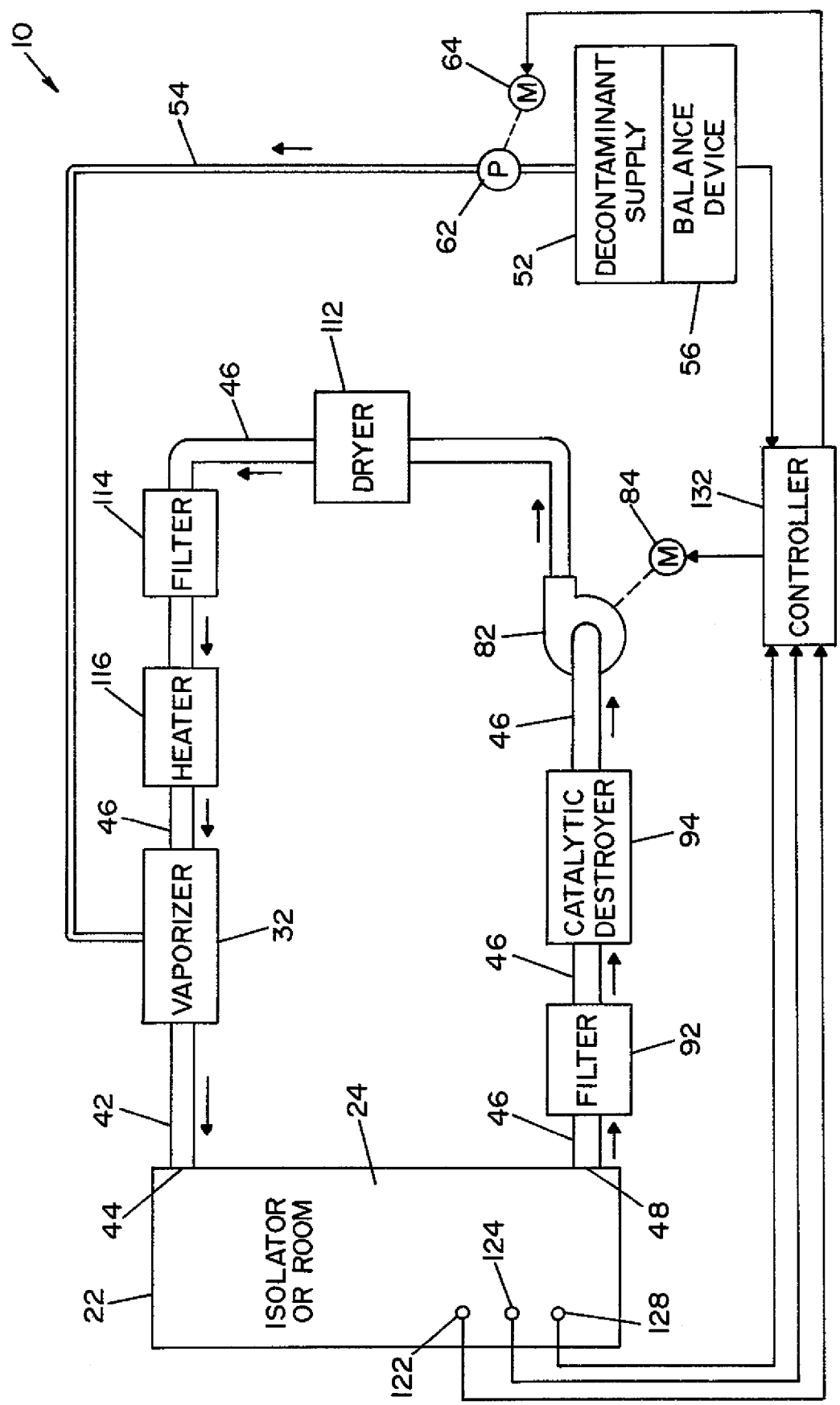
FIG. 1 is a schematic view of a vaporized hydrogen peroxide decontamination system according to a preferred embodiment of the present invention.

Referring now to the drawings wherein the showings are for the purpose of illustrating a preferred embodiment of the invention only, and not for the purpose of limiting same, FIG. 1 shows a vaporized hydrogen peroxide (VHP) decontamination system 10, illustrating a preferred embodiment of the present invention.

In the embodiment shown, system 10 includes an enclosure in the form of an isolator or room 22 that defines a decontamination chamber or region 24. It is contemplated that articles to be sterilized or decontaminated may be disposed within isolator or room 22.

A vaporizer 32 (also referred to as a "generator") is connected to chamber or region 24 of isolator or room 22 by means of a supply conduit 42. Supply conduit 42 defines a fluid inlet 44 to chamber or region 24. Vaporizer 32 is connected to a liquid decontaminant supply 52 by a feed line 54. A conventionally known balance device 56 is associated with decontaminant supply 52, to measure the quantity (i.e., mass) of liquid decontaminant being supplied to vaporizer 32. It is also contemplated that a pressure transducer can be substituted for the balance device to determine the quantity of liquid decontaminant being supplied by decontaminant supply 52 to vaporizer 32. In the illustrated embodiment the liquid decontaminant is an aqueous solution of hydrogen peroxide (e.g., 30% to 59% hydrogen peroxide by weight).

A pump 62, driven by a motor 64, is provided to convey metered amounts of the liquid decontaminant to vaporizer 32 where the decontaminant is vaporized by conventionally known means. As conventionally known, the amount of liquid decontaminant being metered to vaporizer 32 (i.e., the injection rate) can be determined using the measured quantity of liquid decontaminant. Alternatively, pump 62 is provided with an encoder (not shown) that allows monitoring of the amount of decontaminant being metered to vaporizer 32. If an encoder is provided with pump 62, balance device 56 or a pressure transducer is not required.

Isolator or room 22 and vaporizer 32 are part of a circulation system that includes a return conduit 46 that connects isolator or room 22 (and decontamination chamber or region 24) to vaporizer 32. Return conduit 46 defines a fluid outlet 48 to decontamination chamber or region 24. A blower 82, driven by a motor 84, is disposed within return conduit 46 between isolator or room 22 and vaporizer 32. Blower 82 is operable to circulate decontaminant and air. A first filter 92 and catalytic destroyer 94 are disposed in return conduit 46 between blower 82 and isolator or room 22, as illustrated in FIG. 1. First filter 92 is preferably a "high efficiency particulate air" (HEPA) filter and is provided to remove contaminants flowing through system 10. Catalytic destroyer 94 is operable to destroy hydrogen peroxide ($H_2O_2$) flowing therethrough, as is conventionally known. Catalytic destroyer 94 converts hydrogen peroxide ($H_2O_2$) into water ($H_2O$) and oxygen ($O_2$). A dryer 112, a second filter 114 and a heater 116 are disposed within return line 46 between blower 82 and vaporizer 32. Dryer 112 is operable to remove moisture from air blown through the circulation system. For instance, dryer 112 may take the form of a desiccant dryer. Second filter 114 is operable to filter the air blown through return conduit 46 by blower 82. Heater 116 is operable to heat air blown through return conduit 46 by blower 82. In this respect, air is heated prior to entering vaporizer 32. The heated air facilitates vaporization in vaporizer 32.

A humidity sensor 122, a temperature sensor 124, and a hydrogen peroxide ($H_2O_2$) concentration sensor 128 are disposed within chamber or region 24. Humidity sensor 122 is operable to sense the relative humidity (RH) within chamber or region 24. Temperature probe 124 is operable to sense temperature within chamber or region 24. Absolute humidity may be determined from the RH and temperature sensed respectively by humidity sensor 122 and temperature probe 124, or alternatively humidity sensor 122 can take the form of a sensor that directly measures absolute humidity. Hydrogen peroxide concentration sensor 128 takes the form a conventionally known sensing device (e.g., an infrared sensor or electrochemical sensor), and is operable to sense the concentration of hydrogen peroxide within chamber or region 24.

Humidity sensor 122, temperature sensor 124 and hydrogen peroxide concentration sensor 128 provide electrical signals to a system controller 132 that is schematically illustrated in FIG. 1. Controller 132 includes a microprocessor or microcontroller programmed to control the operation of system 10. As illustrated in FIG. 1, controller 132 is also connected to motors 64, 84, and balance device 56. Controller may also include input means (e.g., a keypad or buttons) and output means (e.g., a display, a speaker and/or a printer).

The present invention shall now be further described with reference to the operation of system 10. A typical decontamination cycle includes a drying phase, a conditioning phase, a decontamination phase and an aeration phase. Prior to running a decontamination cycle, data regarding the percentage of hydrogen peroxide in the liquid decontaminant is input into controller 132. As noted above, in a preferred embodiment a decontaminant solution comprised of 35% hydrogen peroxide and 65% water by weight is used. However, a decontaminant solution having different ratios of hydrogen peroxide and water is also contemplated.

Isolator or room 22, supply conduit 42 and return conduit 46 define a conduit circuit. When a decontamination cycle is first initiated, controller 132 causes blower motor 84 to drive blower 82, thereby causing a carrier gas (e.g., air) to circulate through the conduit circuit. During a drying phase, vaporizer 32 is not operating. Dryer 112 removes moisture from the air circulating through the conduit circuit, i.e., through supply conduit 42, return conduit 46 and chamber or region 24 of isolator or room 22, as illustrated by the arrows in FIG. 1. When the air has been dried to a sufficiently low humidity level, the drying phase is complete.

The conditioning phase is then initiated by activating vaporizer 32 and motor 64 of pump 62 to provide metered amounts of the decontaminant solution to vaporizer 32. Within vaporizer 32, the liquid decontaminant is vaporized to produce hydrogen peroxide vapor and water vapor, in a conventionally known manner. The vaporized decontaminant is introduced into the conduit circuit and is conveyed through supply conduit 42 by the carrier gas (i.e., air) into chamber or region 24 of isolator or room 22. During the conditioning phase, hydrogen peroxide vapor is injected into chamber or region 24 at a relatively high rate to bring the hydrogen peroxide concentration level up to a desired level in a relatively short period of time. During the conditioning phase, blower 82 causes air to continuously circulate through the circulation system. As vaporized hydrogen peroxide enters chamber or region 24 from vaporizer 32, vaporized hydrogen peroxide is also being drawn out of chamber or region 24 through catalytic destroyer 94 where it is broken down into water and oxygen.

After the conditioning phase is completed, the decontamination phase is initiated. During the decontamination phase, the decontaminant injection rate to vaporizer 32 and to chamber or region 24 is decreased to maintain the hydrogen peroxide concentration substantially constant at a desired level. The decontamination phase is run for a predetermined period of time, preferably with the hydrogen peroxide concentration remaining substantially constant at a desired level, for a predetermined period of time that is sufficient to effect the desired decontamination of chamber or region 24, and objects located therein.

After the decontamination phase is completed, controller 132 causes vaporizer 32 to shut down, thereby shutting off the flow of vaporized hydrogen peroxide into chamber or region 24.

Thereafter, the aeration phase is run to bring the hydrogen peroxide level down to an allowable threshold (e.g., about 1 ppm or less). In this respect, as will be appreciated, blower 82 continues to circulate the air and vaporized decontaminant through the circulation system, thereby causing the last of the vaporized hydrogen peroxide (VHP) to be broken down by catalytic destroyer 94.

Throughout the respective operational phases, humidity sensor 122, temperature probe 124, and hydrogen peroxide concentration sensor 128 respectively monitor the relative humidity (RH), temperature, and hydrogen peroxide concentration within chamber or region 24, and provide electrical signals to controller 132 indicative of the relative humidity, temperature, and hydrogen peroxide concentration. Controller 132 determines the absolute humidity (AH) from the relative humidity (RH) and temperature, as is conventionally known. Alternatively, as described above, humidity sensor 122 may take the form of a sensor that directly measures absolute humidity.

In accordance with the present invention, controller 132 is programmed to provide "feedback control." As will be described in detail below, feedback control is used to prevent condensation of hydrogen peroxide within chamber or region 24 during the decontamination cycle, and to operate system 16 more efficiently in order to minimize the decontamination cycle time (i.e., the total time required to complete a successful decontamination cycle).

Feedback control will now be described in detail with reference to FIG. 2. At least one hydrogen peroxide concentration level and one "D value" are programmed into controller 132 by an operator of system 10. In the illustrated embodiment, two (2) hydrogen peroxide ($H_2O_2$) concentration levels (e.g., a low concentration level (e.g., 250 ppm) and a high concentration level (e.g., 400 ppm)) are programmed into controller 132. In accordance with the programmed "D value," controller 132 determines a required exposure time for each programmed $H_2O_2$ concentration level, in a conventionally known manner. The exposure time is the minimum required time for exposure to the decontaminant (i.e., hydrogen peroxide) in order to effect decontamination. It is also contemplated that an operator may alternatively program into controller 132 at least one hydrogen peroxide concentration level and exposure time associated therewith.

Controller 132 is also programmed with a dew point margin ($\Delta_{MARGIN}$). The dew point margin ($\Delta_{MARGIN}$) is a delta value that is indicative of the minimum acceptable difference between: (1) the actual $H_2O_2$ concentration (as sensed by $H_2O_2$ concentration sensor 128) and (2) the dew point concentration for the hydrogen peroxide vapor ($C_{DP}$), as calculated by controller 132. As will be explained below, the dew point margin ($\Delta_{MARGIN}$) is used to prevent system 10 from operating in a manner wherein the actual $H_2O_2$ concentration ($C_{ACTUAL}$) exceeds the dew point concentration for the hydrogen peroxide vapor ($C_{DP}$). As a result, condensation of hydrogen peroxide inside chamber or region 24 is prevented.

During the conditioning and decontamination phases of the decontamination cycle, controller 132 will control system 10 to prevent condensation of hydrogen peroxide within chamber or region 24. In this regard, controller 132 uses data provided by humidity sensor 122 together with data provided by temperature probe 124 (measuring temperature), to calculate the absolute humidity within chamber or region 24. As indicated above, humidity sensor 122 may alternatively take the form of a sensor that directly measures absolute humidity. Using the absolute humidity, controller 132 determines in a conventionally known manner the dew point concentration for the hydrogen peroxide vapor ($C_{DP}$), at the temperature inside chamber or region 24. Controller 132 also monitors the actual $H_2O_2$ concentration ($C_{ACTUAL}$) inside chamber or region 24 using $H_2O_2$ concentration sensor 128.

Controller 132 determines a measured delta value ($\Delta_{MEASURED}$) that is the difference between: (1) the actual $H_2O_2$ concentration ($C_{ACTUAL}$) inside chamber or region 24 and (2) the dew point concentration for the hydrogen peroxide vapor ($C_{DP}$). If the measured delta value ($\Delta_{MEASURED}$) is less than the dew point margin ($\Delta_{MARGIN}$), then the actual $H_2O_2$ concentration ($C_{ACTUAL}$) is approaching too closely the dew point concentration for the hydrogen peroxide vapor ($C_{DP}$). Accordingly, controller 132 takes appropriate action to increase the measured delta value ($\Delta_{MEASURED}$) to a value greater than the dew point margin ($\Delta_{MARGIN}$). In the illustrated embodiment, controller 132 increases the measured delta value ($\Delta_{MEASURED}$) to a value greater than the dew point margin ($\Delta_{MARGIN}$) by decreasing the injection rate of the aqueous solution of hydrogen peroxide to vaporizer 32, thereby reducing the actual $H_2O_2$ concentration ($C_{ACTUAL}$) inside chamber or region 24.

In one embodiment of the present invention, a plurality of humidity sensors 122 and $H_2O_2$ concentration sensors 128 may be located within chamber or region 24 to provide data signals to controller 132. The plurality of sensors 122 and 128 may be located at different locations within chamber or region 24. In this embodiment, controller 132 preferably determines the dew point margin ($\Delta_{MARGIN}$) using (data from the $H_2O_2$ concentration sensor 128 indicative of the highest actual $H_2O_2$ concentration ($C_{ACTUAL}$). Similarly, controller 132 preferably uses the data from the $H_2O_2$ concentration sensor 128 indicative of the lowest actual $H_2O_2$ concentration ($C_{ACTUAL}$) when determining an elapsed or total exposure time associated with a vaporized decontaminant. Controller 132 also preferably determines the dew point concentration (i.e., saturation concentration) for the hydrogen peroxide vapor ($C_{DP}$) based upon data from the humidity sensor 122 indicative of the lowest dew point concentration for the hydrogen peroxide vapor ($C_{DP}$).

As indicated above, two (2) hydrogen peroxide ($H_2O_2$) concentration levels (i.e., a low $H_2O_2$ concentration level (e.g., 250 ppm) and a high $H_2O_2$ concentration level (e.g., 400 ppm)) are programmed into controller 132. If controller 132 is operating system 10 at the programmed high $H_2O_2$ concentration level when controller 132 determines that the measured delta value ($\Delta_{MEASURED}$) is less than the dew point margin ($\Delta_{MARGIN}$), then controller 132 begins operating system 10 at the programmed low $H_2O_2$ concentration level Controller 132 adjusts the exposure time so that it corresponds to the programmed low $H_2O_2$ concentration level. If controller 132 is operating system 10 with the programmed low $H_2O_2$ concentration level when controller 132 determines that the measured delta value ($\Delta_{MEASURED}$) is less than the dew point margin ($\Delta_{MARGIN}$), then controller 132 can provide an audible or visual signal alerting the operator to this condition and/or abort the decontamination cycle. If the decontamination cycle is aborted, the injection rate of the vaporized hydrogen peroxide is reduced to zero.

Figure 2:
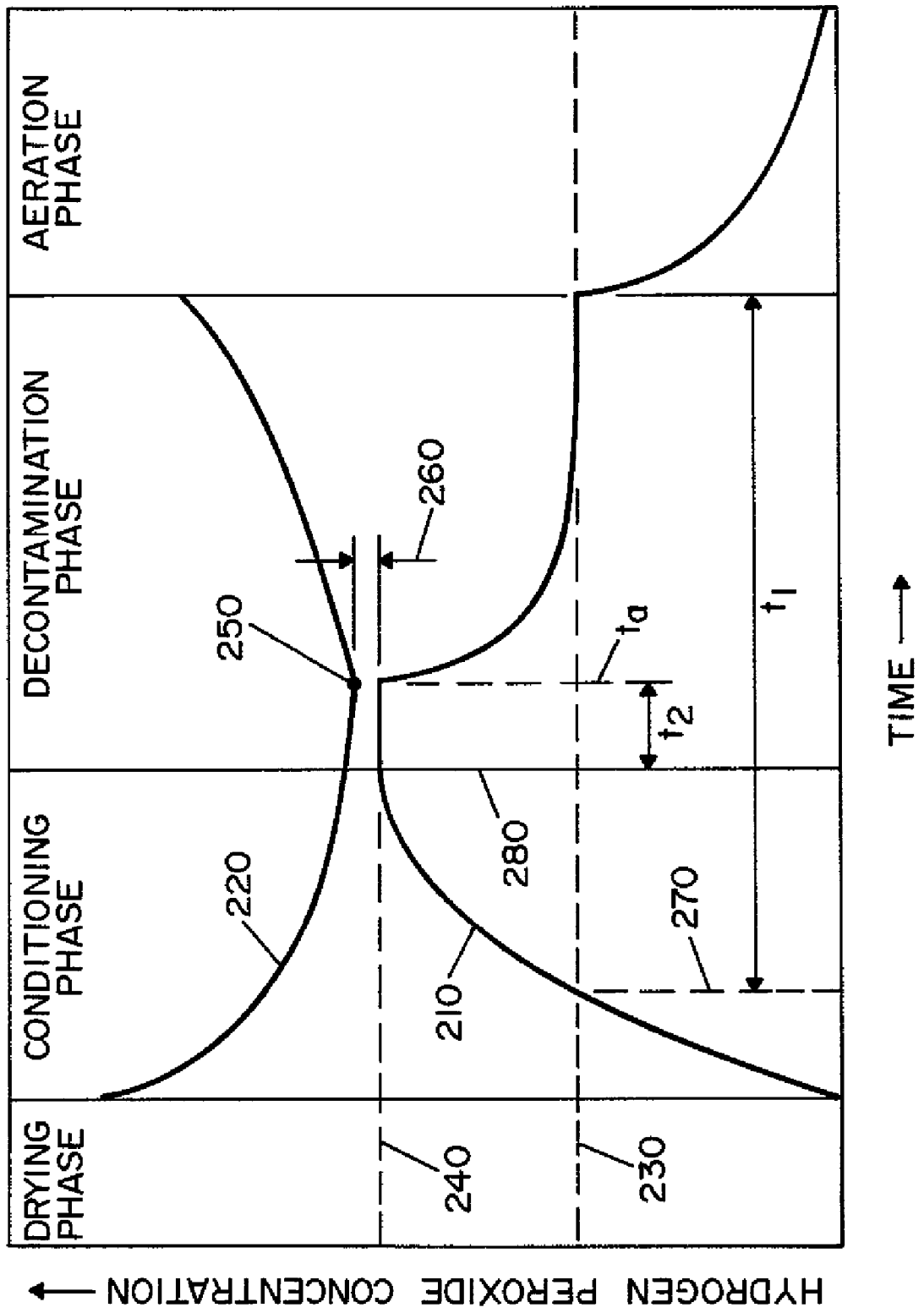
FIG. 2 is a graph depicting a decontamination cycle of the decontamination system shown in FIG. 1

Referring now to FIG. 2, a graph depicting the four (4) phases of a decontamination cycle is shown and illustrates the relationship between the actual $H_2O_2$ concentration ($C_{ACTUAL}$), and the dew point concentration for the hydrogen peroxide vapor ($C_{DP}$) during the conditioning and decontamination phases. In FIG. 2, the actual $H_2O_2$ concentration ($C_{ACTUAL}$) is designated by line 210, and the dew point concentration for the hydrogen peroxide vapor ($C_{DP}$) is designated by line 220. Initially, controller 132 is programmed to operate system 10 with the programmed high $H_2O_2$ concentration level (e.g., 400 ppm), designated by dashed line 240. During the conditioning phase, the actual $H_2O_2$ concentration ($C_{ACTUAL}$) increases, while the dew point concentration for the hydrogen peroxide vapor ($C_{DP}$) decreases. During the decontamination phase, the values for $C_{ACTUAL}$ and $C_{DP}$ (see reference number 250) move closer to each other, such that the measured delta value ($\Delta_{MEASURED}$), as designated by reference number 260, decreases to a value wherein the measured delta value ($\Delta_{MEASURED}$) is less than the dew point margin ($\Delta_{MARGIN}$). Consequently, at time $t_a$, controller 132 changes operation of system 10 from the programmed high $H_2O_2$ concentration level to the programmed low $H_2O_2$ concentration level (e.g., 250 ppm), designated by dashed line 230. As a result, the measured delta value ($\Delta_{MEASURED}$) increases, as the actual $H_2O_2$ concentration ($C_{ACTUAL}$) decreases and the dew point concentration for the hydrogen peroxide vapor ($C_{DP}$) increases.

In accordance with the present invention, controller 132 is also programmed to operate first and second timers for determining exposure time during operation of system 10. The first timer is used to monitor the actual exposure time for the programmed low $H_2O_2$ concentration level (250 ppm) and the second timer is used to monitor the actual exposure time for programmed high $H_2O_2$ concentration level (400 ppm). Accordingly, the first timer is started when the actual $H_2O_2$ concentration ($C_{ACTUAL}$) has reached the programmed low $H_2O_2$ concentration level (as designated by dashed line 270), and continues timing as long as the actual $H_2O_2$ concentration ($C_{ACTUAL}$) remains at, or above, the programmed low $H_2O_2$ concentration level. The second timer is started when the actual $H_2O_2$ concentration ($C_{ACTUAL}$) has reached the programmed high $H_2O_2$ concentration level (as designated by line 280), and continues timing as long as the actual $H_2O_2$ concentration ($C_{ACTUAL}$) remains at, or above, the programmed high $H_2O_2$ concentration level. In FIG. 2, $t_1$ represents the elapsed time for the first timer and $t_2$ represents the elapsed time for the second timer.

A decontamination cycle is determined to have been successfully completed when the $H_2O_2$ concentration level has been maintained within chamber or region 24 for the exposure time associated with the $H_2O_2$ concentration level. As discussed above, the required exposure time corresponding to a given $H_2O_2$ concentration level is directly programmed into controller 132 or is determined from a programmed D-value. If controller 132 has been programmed to operate system 10 at the high $H_2O_2$ concentration level, but system 10 is unable to achieve the high $H_2O_2$ concentration level, then controller 132 will automatically switch to operating system 10 at the low $H_2O_2$ concentration level. The high $H_2O_2$ concentration level may not be achievable because the maximum injection rate is insufficient to obtain the high $H_2O_2$ concentration level, or controller 132 may determine that the measured delta value ($\Delta_{MEASURED}$) is less than the dew point margin ($\Delta_{MARGIN}$), thereby indicating that the actual $H_2O_2$ concentration ($C_{ACTUAL}$) has too closely approached the dew point concentration for the hydrogen peroxide vapor ($C_{DP}$). As illustrated in FIG. 2, $C_{ACTUAL}$ (line 210) too closely approaches $C_{DP}$ (line 220) at time $t_a$.

In some cases, the high $H_2O_2$ concentration level may be achievable, but the time required to reach the high $H_2O_2$ concentration level may be relatively long. Accordingly, controller 132 determines whether it is faster to modify the operation of system 10 to operate at the low $H_2O_2$ concentration level. In this respect, controller 132 compares the remaining exposure time needed to complete a successful decontamination cycle at the low $H_2O_2$ concentration level (taking into consideration the current value of the first timer) with the required exposure time needed to complete a successful decontamination cycle at the high $H_2O_2$ concentration level. If controller 132 determines that a successful decontamination cycle can be completed sooner at the low $H_2O_2$ concentration level, then controller 132 will reduce the $H_2O_2$ concentration level in chamber or region 24 to the programmed low $H_2O_2$ concentration level for the remaining duration of the decontamination cycle. Therefore, controller 132 will operate at the low $H_2O_2$ concentration level for the duration of a decontamination cycle when it is determined that the time remaining to complete a successful decontamination cycle at the low $H_2O_2$ concentration level is less than (or equal to) the time remaining to complete a successful decontamination cycle at the high $H_2O_2$ concentration level. Accordingly, controller 132 will operate at the low concentration level for the duration of a decontamination cycle if:

$$T_L - t_1 \leq T_H - t_2$$

where $T_L$=total exposure time required at the low $H_2O_2$ concentration level,
$T_H$=total exposure time required at the high $H_2O_2$ concentration level,
$t_1$=elapsed exposure time at the low $H_2O_2$ concentration level, and
$t_2$=elapsed exposure time a the high $H_2O_2$ concentration level.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, in the illustrated embodiment of the present invention, the liquid decontaminant is an aqueous solution of hydrogen peroxide. It is contemplated that the present invention may find advantageous application with decontamination systems using other gas or vapor-phase decontaminants. In such alternative embodiments, the saturation concentration of interest will be the saturation concentration of the other vapor-phase decontaminants. Furthermore, it is also contemplated that the present invention may be modified to permit condensation of hydrogen peroxide vapor at very low levels (i.e., "micro-condensation") in order to provide a layer of hydrogen peroxide directly to the surfaces to be treated. It is intended that all such modifications and alterations be included insofar as they come within the scope of the invention as claimed or the equivalents thereof.

Having described the invention, the following is claimed:

1. A vapor decontamination system for decontaminating a region, said system comprising:
   a generator for generating a vaporized decontaminant;
   a circulating system for supplying said vaporized decontaminant to said region;
   at least one humidity sensor providing a first signal indicative of moisture in the region;
   a temperature sensor providing a second signal indicative of the temperature in the region;
   at least one concentration sensor providing a third signal indicative of the concentration of the decontaminant in the region;
   a controller communicating with said generator to control the rate at which vaporized decontaminant is injected into the region, said controller receiving the first, second, and third signals, a first concentration level for the vaporized decontaminant, and a second concentration level for the vaporized decontaminant, wherein said first and second concentration levels have respective first and second exposure times associated therewith, said first concentration level being greater than said second concentration level;
   first means for timing to provide an indication of the total time that the actual concentration of the vaporized decontaminant in the region is at or above the first concentration level;
   second means for timing to provide an indication of the total time that the actual concentration of the vaporized decontaminant in the region is at or above the second concentration level;
   wherein said controller is programmed to:
      inject the vaporized decontaminant generated by the generator into the region at a first injection rate for obtaining the first concentration level of the vaporized decontaminant in the region;
      monitor the actual concentration of the vaporized decontaminant in the region using the at least one concentration sensor;
      determine the dew point concentration of the vaporized decontaminant in the region;
      determine whether the actual concentration of the vaporized decontaminant in the region is at least a predetermined amount below the dew point concentration of the vaporized decontaminant in the region; and
      reduce the injection rate of the vaporized decontaminant from the first injection rate for obtaining the first concentration level of the vaporized decontaminant to a second injection rate for obtaining the second concentration level of the vaporized decontaminant, if (1) the actual concentration of the vaporized decontaminant in the region is not at least the predetermined amount below the dew point concentration of the vaporized decontaminant in the region or (2) the amount of time indicated by the second means for timing to reach the second exposure time is less than the amount of time indicated by the first means for timing to reach the first exposure time.

2. A vapor decontamination system according to claim 1, wherein said controller receives, via input means, one of: (a) said first concentration level and said first exposure time associated therewith, or (b) said first concentration level and a D-value indicative of a desired reduction of bioburden, wherein said first exposure time associated with said first concentration level is determined according to the D-value.

3. A system according to claim 1, wherein said controller receives, via input means, one of: (a) said second concentration level and said second exposure time associated therewith, or (b) said second concentration level and a D-value indicative of a desired reduction of bioburden, wherein said second exposure time associated with said second concentration level is determined according to the D-value.

4. A system according to claim 1, wherein said controller is further programmed to reduce the injection rate of the vaporized decontaminant to zero, when the injection rate of the vaporized decontaminant is at said second injection rate for obtaining said first concentration level of the vaporized decontaminant and the actual concentration of the vaporized decontaminant in the region is not at least the predetermined amount below the dew point concentration of the vaporized decontaminant in the region.

5. A system according to claim 1, wherein said system further comprises:
   at least one of an audible indicator or a visual indicator, said indicator being activated by said controller if the actual concentration of the vaporized decontaminant in the region is not at least the predetermined amount below the dew point concentration of the vaporized decontaminant in the region.

6. A system according to claim 1, wherein said controller is further programmed to determine whether the actual concentration of the vaporized decontaminant in the region is at least the predetermined amount below the dew point concentration of the vaporized decontaminant in the region by:
   establishing a dew point margin indicative of a minimum acceptable difference between: (1) actual concentration of the vaporized decontaminant in the region and (2) dew point concentration of the vaporized decontaminant in the region;
   determining a measured delta value indicative of the difference between the actual concentration of the vaporized decontaminant and the dew point concentration for the vaporized decontaminant; and
   comparing the measured delta value to the dew point margin.

7. A system according to claim 1, wherein said vaporized decontaminant is generated from an aqueous solution of hydrogen peroxide.

8. A system according to claim 1, wherein said system comprises a plurality of concentration sensors indicating the concentration of the decontaminant in the region, wherein data from the concentration sensor indicating the highest concentration of the vaporized decontaminant in the region is used by the controller to determine whether the actual concentration of the vaporized decontaminant in the region is at least a predetermined amount below the dew point concentration of the vaporized decontaminant in the region.

9. A system according to claim 1, wherein said system comprises a plurality of concentration sensors indicating the concentration of the decontaminant in the region, wherein data from the concentration sensor indicating the lowest concentration of the decontaminant is used to operate said first and second means for timing that respectively provide an indication of the total time that the actual concentration of the vaporized decontaminant in the region is at or above the first and second concentration levels.

10. A system according to claim 1, wherein said system comprises a plurality of humidity sensors, said controller determining the dew point concentration using data from the humidity sensor indicative of the lowest dew point concentration.

* * * * *